United States Patent [19]

Relenyi et al.

[11] Patent Number: 5,118,534
[45] Date of Patent: Jun. 2, 1992

[54] ALKYLTHIOETHANAMINE CARBAMIC ACID DERIVATIVES AND THEIR USE IN BIOCIDAL COMPOSITIONS

[75] Inventors: Attila G. Relenyi; Richard W. Walter; Charles D. Gartner, all of Midland, Mich.

[73] Assignee: The Dow Chemical Company, Midland, Mich.

[21] Appl. No.: 651,892

[22] Filed: Feb. 7, 1991

[51] Int. Cl.$^5$ ................................. B05D 3/02
[52] U.S. Cl. ..................... 427/384; 514/665; 562/555
[58] Field of Search .......... 514/665; 562/555; 427/384

[56] References Cited

U.S. PATENT DOCUMENTS

| | | | |
|---|---|---|---|
| 3,291,683 | 12/1966 | Lamb | 167/22 |
| 3,524,719 | 7/1970 | Wolf et al. | 252/390 |
| 4,074,998 | 2/1978 | Lacefield | 71/66 |
| 4,102,801 | 7/1978 | Brodoway | 252/182 |
| 4,698,173 | 10/1987 | Hansen | 562/555 X |
| 4,816,061 | 3/1989 | Walter, Jr. et al. | 75/67 |
| 4,970,239 | 11/1990 | Whitekettle et al. | 514/665 |
| 5,008,261 | 4/1991 | Kruger et al. | 562/555 X |

Primary Examiner—Michael Lusignan

[57] ABSTRACT

Alkylthioalkylamine carbamic acid derivatives are prepared which correspond to the formula:

$$RS(CH_2)_m\overset{+}{N}H_3\overset{-}{O}-\overset{O}{\overset{\|}{C}}NH(CH_2)_nSR_1 \quad (I)$$

wherein R and $R_1$ are both independently alkyl groups containing from 6 to 16 carbon atoms, and m and n are both independently integers of from 2 or 3. Compositions containing these compounds inhibit the growth of organisms such as bacteria, yeast, fungi, mold, algae, mollusks, hydroids, or tunicates on surfaces.

16 Claims, No Drawings

ALKYLTHIOETHANAMINE CARBAMIC ACID DERIVATIVES AND THEIR USE IN BIOCIDAL COMPOSITIONS

BACKGROUND OF THE INVENTION

This invention relates to a novel compound, and a method of its use for inhibiting the growth of microorganisms and marine organisms on surfaces.

Problems associated with growth of yeast, mold, fungi, bacteria, and algae on surfaces like shower stalls include discoloration and possibly unsanitary surfaces. Current market cleaners which "bleach" out discoloration leave little or no residual cleaner to prevent rapid re-growth of organisms.

It would be greatly desirable to have a commercially acceptable composition and method of use of the composition to inhibit the growth of such microorganisms and marine organisms by employing an in-situ produced or pre-prepared antimicrobial film layer, which remains on the surface for a considerable length of time.

Alkylthioethylamines and related alkylaminosulfides are known for their bactericidal activity. Fungi and bacteria have been controlled by use of alkylthioalkylamines and dithiocarbamates, whereas aquatic weeds have been controlled by phenylthioalkylamines.

U.S. Pat. No. 4,816,061 to Walter, Jr., et al., teaches the use of alkylthioalkylamines for inhibiting microorganisms and/or controlling biofouling of cooling towers.

Alkali metal carbamates of amines have been used as antioxidants for lubricants, whereas polyamine carbamates have been found useful as vulcanizing agents for fluororubbers.

The desirability of identifying or discovering new antimicrobial agents is widely recognized for several reasons. These include the development of microbe strains resistant to known antimicrobials, the occurrence of undesirable interactions of certain known antimicrobials with the medium or product in which the antimicrobial is used, and high toxicity of certain known antimicrobials to certain non-target organisms such as mammals.

The present invention solves this problem by disclosing a new compound which may be employed as an antimicrobial for inhibiting the growth of microorganisms or marine organisms on surfaces.

SUMMARY OF THE INVENTION

The present invention is directed to a compound corresponding to the formula:

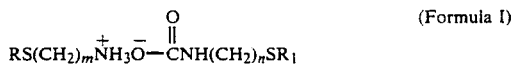
(Formula I)

wherein R and R$_1$ are both independently alkyl groups containing from 6 to 16 carbon atoms, and m and n are both independently integers selected from 2 or 3.

The present invention is also directed to a method for inhibiting the growth of microorganisms and marine organisms on a surface which comprises applying to said surface (i) a first compound corresponding to the following formula:

RS(CH$_2$)$_m$NH$_2$ (Formula II)

wherein R is an alkyl group containing from 6 to 16 carbon atoms and m is an integer selected from 2 or 3, and (ii) a second compound corresponding to the formula:

R$_1$S(CH$_2$)$_n$NH$_2$ (Formula IIa)

wherein R1 is an alkyl group containing from 6 to 16 carbon atoms and n is an integer selected from 2 or 3 and wherein the surface is exposed to air during application of the compounds. The first and second compounds are applied in amounts effective to inhibit the growth of microorganisms and marine organisms on the surface and whereby a film of the compound of formula:

(Formula I)

wherein R,R$_1$, m and n are as defined hereinabove, is formed on the surface.

In another aspect, the present invention relates to the method of use of the compound of Formula I for inhibiting growth of microorganisms and marine organisms on a surface which comprises introducing onto said surface a compound corresponding to the formula:

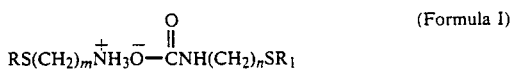
(Formula I)

wherein R and R$_1$ are both independently alkyl groups containing from 6 to 16 carbon atoms, and m and n are both independently integers selected from 2 or 3 and wherein the compound is introduced in an amount effective to inhibit the growth of microorganisms and marine organisms on the surface. "Introducing onto said surface" is intended to encompass either applying the compound directly onto the surface or applying to the surface precursors of the compound which react to form the compound.

DETAILED DESCRIPTION OF THE INVENTION

This invention relates to a compound corresponding to the formula:

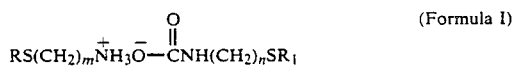
(Formula I)

wherein R and R$_1$ are both independently alkyl groups containing from 6 to 16 carbon atoms, and m and n are both independently integers of from 2 or 3.

In the compounds of Formula I, it is preferred that m or n is 2. It is also preferred that R and R1 are both independently alkyl groups containing from 6 to 12 carbon atoms. The most preferred compound is n-decylthioethylaminecarbamic acid derivative, wherein both R and R1 are decyl groups and m and n are each the integer 2.

In the present specifications and claims, the term "alkyl" is employed to designate straight and branched chain alkyls. Preferably, the term "alkyl" is employed to designate straight chain alkyls of 6 to 16 carbon atoms and branched chain alkyls of 6 to 16 carbon atoms. More preferably, the term "alkyl" is employed to designate straight chain alkyls of 6 to 12 carbon atoms and branched chain alkyls of 6 to 12 carbon atoms.

As used herein, the term "film" refers to a covering or a layer of the compounds of the Formula I or of the Formula II on to a surface exposed to air. Such a film should be at least one molecule thick and may be as thick as 1 millimeter (mm).

As used herein, the term "adventitious carbon dioxide" refers to that carbon dioxide which is not inherent or innate to the compound of Formula II or IIa or a mixture of compounds of Formula II and IIa, but instead is added from an external source, which in the present invention could be the atmospheric carbon dioxide.

As used herein, the term "effective amount" refers to that amount of a compound or a mixture of two or more compounds of this invention, which is needed to exhibit inhibition or killing of selected organisms. Typically, this amount varies from about 1 part per million (ppm) to about 100,000 ppm by weight of the formulation. Such amounts vary depending upon the particular compound tested, the targeted organisms and the amount of formulation to be applied to a given area. Also, the exact concentration of the compounds to be added in the treatment of industrial and consumer formulations may vary within a product type depending upon the components of the formulation.

As used herein, the term "inhibit" refers to suppression, control, stasis, killing, retardation or any other interference with the normal life processes of microorganisms such as algae, bacteria, yeast, molds, and marine organisms such as mollusks, hydroids, tunicates, and the like.

Structural Formula of carbamic acid derivative of alkylthioialkylamine

In the following discussion, $R_2$ and $R_3$ simply represent generic alkyl groups.

The chemical structure of the reaction product of aliphatic amine with carbon dioxide has been reported in U. Mioc and S. Ribnikar (Bull. de la Soc. Chim. Beograd 43 (9), 603—612 (1987), incorporated herein by reference, to be a carbamic acid having the structure as illustrated in the following equation:

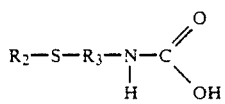

Mioc et.al (Bull. de la Soc. Chim. Beograd, 43 (10), 725-732 (1978) incorporated herein by reference have proposed that the carbamic acid, formed in the reaction of aliphatic amine with carbon dioxide, forms an acid-base pair with the free amine in the reaction mixture as illustrated by the following formula:

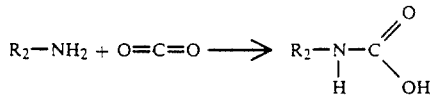

By analogy, the initially formed product of the reaction of alkylthioalkylamine with carbon dioxide in the present invention is envisaged to be an alkylthioalkylcarbamic acid represented by Formula III:

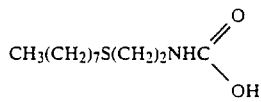

The carbamic acid so produced then, presumably, reacts further with the free amine to give the carbamic acid derivative similar to the compound of Formula I:

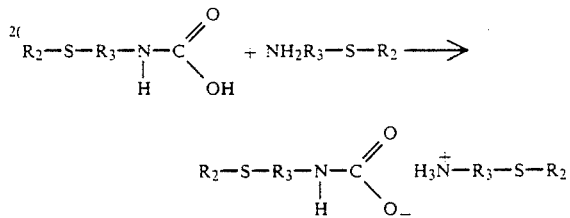

The carboxylation of 2-(octylthio)ethanamice in the present invention presumably yields an intermediate carbamic acid of formula:

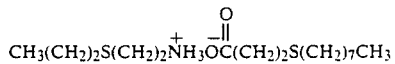

The carbamic acid then reacts with another molecule of 2-(octylthio)ethanamine to yield 2-(octylthio)ethanamine carbamic acid derivative of formula:

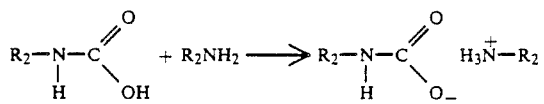

The structure of the carbamic acid derivative as obtained above has been characterized by carbon nuclear magnetic resonance spectroscopy (NMR), infrared spectroscopy (IR), and elemental analysis and is consistent with the above formula.

Preparation

Methods of preparation of the alkylthioalkylamines of Formula II and IIa are known in the art, for example, in U.S. Pat. Nos. 3,291,363 and 3,524,719, incorporated herein by reference. They can also be prepared by reacting ethyl oxazoline with a mercaptan i.e., an aliphatic thiol, such as "RSH", with subsequent hydrolysis of the resultant amide to yield the desired amine. Ethyl oxazolines and mercaptans are commercially available for use as starting materials.

Carboxylation of alkylthioalkylamines of Formula II and IIa to yield alkylthioalkylcarbamic acid derivatives is achieved by bubbling carbon dioxide gas through an acetonitrile solution of alkylthioalkylamine to afford a white precipitate which is recovered by known methods such as suction filtration, centrifugation or similar solid recovery from a heterogeneous mixture.

Method of Use

The method of this invention can be practiced by applying an effective amount of a solution, a slurry, a suspension, a paste or a solid composition of preprepared carbamic acid derivatives of Formula I to surfaces such as shower stalls, paints, walls, tiles, ships, or pilings, where biocidal activity is desired.

A solution of solid carbamic acid derivatives can be obtained by dissolving the compounds of Formula I into polar aprotic solvents like dimethylformamide.

A solid formulation of carbamic acid derivatives of Formula I can be obtained by mixing the carbamic acid derivative with solid fillers such as calcium carbonate. A suspension of the carbamic acid derivatives can be prepared by suspending the carbamic acid derivative in solvents in which the carbamic acid derivative is sparingly soluble and such suspensions can then be made into pastes or slurries by use of thickeners such as cellulose ethers.

In another embodiment of this invention, an effective amount of at least one amine corresponding to each of the Formula II or Formula IIa is applied in the form of a solution, a slurry, a suspension, a paste, a liquid, or a spray, to a surface of choice exposed to air at the time of application of the amines. The amines of Formula II and Formula IIa can be the same or different. The solutions of the free amines can be formed by dissolving the free amines of Formula II or IIa into solvents, such as methylene chloride or acetonitrile. A paste or a slurry of the free amine may be obtained by mixing liquid alkylthioalkylamines with thickeners such as cellulose ethers. The free amine can also be dispersed in an aerosol material, such as a fluorinated hydrocarbon or other propellant, for use as a spray. In addition to a solvent, diluent or dispersing agent, other adjuvants such as pigments, viscosity modifiers and surface active agents may be present in the formulation.

A preferred application is for the production of biocidal foams since the amine can readily be incorporated into a blowing agent such as methylene chloride along with air.

The free amines on application to a surface will react in-situ with adventitious carbon dioxide present in the atmosphere to produce at least one carbamic acid derivative which then acts as a biocidal matrix. The carbamic acid derivative typically remains on the surface for at least five days, depending upon the nature of the surface treated and the uses made of the surface after the application of a film. Either the compound corresponding to formula I, a mixture of compounds of formula II and IIa, or at least one compound corresponding to formula II or IIa can be applied in an amount effective to retard the growth of microorganisms or marine organisms as the situation warrants.

Another application of the present invention is in paint formulations. The amine can react with adventitious carbon dioxide to form a non-leaching film during the process of paint film formation regardless of paint film formation mechanism.

The following examples are to further illustrate the present invention but should not be interpreted as a limitation thereon.

EXAMPLE I

Synthesis of 2-(octylthio)ethyl propionamide 1200 g (12.1 moles) of 2-ethyl-2-oxazoline and 1771 g (12.1 moles) of 1-octanethiol are mixed in a large beaker and charged into a 5 liter round-bottom flask swept with dry nitrogen. 3.944 g (28.9 mmoles) of powdered zinc chloride catalyst are added, and the mixture heated at 170° C. for about four hours to afford a straw-yellow crude oil which solidifies at about 40° C. Fractional distillation gives 2,849 g (yield, 96%) of a clear oil, b.p. 166°–179° C. (0.2–0.3 mmHg), which solidifies upon cooling to a white, waxy, crystalline solid (m.p. 37°–38° C.). The structure identity is confirmed by IR, proton NMR, and elemental analysis.

Hydrolysis of 2-(octylthio)ethyl propionamide to yield 2-(octylthio)ethanamine

A liquid (50° C.) melt of n-octylthioethyl propionamide (804.6 g, 3.28 moles) is added to 750 ml of concentrated (36.6%) aqueous hydrochloric acid solution in a jacketed 4-liter glass reactor. The stirred mixture is heated to about 90° C. for about 72 hours. The resulting hot solution is brought to a pH of about 13 with about 400 ml of 12M aqueous potassium hydroxide solution, while maintaining the temperature between 60°–90° C. After bringing the solution to a pH of 13 and allowing it stand unstirred for about ½ hour, a dark brown organic phase cleanly separates as the upper phase which is recovered for subsequent distillation.

Fractional distillation under nitrogen gives 527 g (yield, 71.2%) of a clear oil, b.p. 125°–127° C. (0.3 mmHg), which is identified by IR, proton NMR, and elemental analysis.

Carboxylation of 2-(octylthio)ethanamine to yield a carbamic acid derivative

Carbon dioxide is bubbled through an acetonitrile (60 ml) solution of 10 g (52.8 mmoles) of 2-(octylthio)ethylamine to afford a white precipitate which is isolated by suction filtration. The product is washed three times with 10 ml portions of acetonitrile and is then washed three times with 20 mls portions of methyl t-butyl ether. The product is air dried to give 7.77 g of octylthioethylamine carbamic acid derivative as a white powder (yield, 62.1%). The product is further characterized by IR, proton NMR, and elemental analysis.

EXAMPLE II

Synthesis of 2-(decylthio)ethanamine hydrochloride

Approximately 225 pounds of decylmercaptan are loaded into a jacketed reactor equipped with an agitator. 1.25 pounds of zinc chloride catalyst are added through the manhole. The system is heated to approximately 140° C. and 130 pounds of 2-ethyl-2-oxazoline are added at the rate of 3 lbs/min in about 45 minutes. About 30 minutes are allowed for the reaction to be completed, the reactor cooled to approximately 120° C. and 155 pounds of 32 weight percent hydrochloric acid are then added to the reaction mixture. The reactor is heated to 150°–160° C., at which time the vapor pressure of the system is approximately 60 psi. The temperature is maintained near 150° C. for 2 hours to complete the hydrolysis.

Synthesis of 2-(decylthio)ethanamine

After the hydrolysis in the above step is complete, the reactor is cooled to about 100° C. and approximately 2.0 equivalents of sodium hydroxide (217 lbs of 50 weight percent solution), based upon the hydrochloric acid added in the production of 2-(decylthio)ethanamine hydrochloride, are introduced with stirring in approximately 30 minutes. The reaction mixture is allowed to settle until phase separation is complete (approximately 30 minutes) and the 2-(decylthio)ethanamine is decanted off. The 2-(decylthio)ethanamine can be passed over a drying agent such as sodium sulfate, or may be vacuum stripped to remove any dissolved and/or entrained water.

2-(decylthio)ethanamine can also be recovered from the reaction mixture by extraction with a water immiscible organic solvent such as toluene or methylene chloride The resulting solution can be decanted off from the aqueous phase and dried in the manner described herein above.

Synthesis of the carbamic acid derivative of 2-(decylthio)ethanamine

The carbamic acid salt of 2-(decylthio)ethanamine can be prepared by bubbling carbon dioxide gas into the organic solution of 2-(decylthio)ethanamine obtained as described herein above.

The carbamic acid salt of 2-(decylthio)ethanamine can also be prepared by pouring 2-(decylthio)ethanamine to form a film and exposing the film to adventitious carbon dioxide or to carbon dioxide from evaporation of dry ice. The carbon dioxide reacts with the amine to produce carbamic acid derivative of 2-(decylthio)ethanamine.

The carbamic acid derivative can also be prepared by spraying 2-(decylthio)ethanamine as a mist into a chamber containing carbon dioxide to form the carbamic acid salt of 2-(decylthio)ethanamine.

Biocidal Activity

The compounds of the present invention are useful because of their biocidal activity and can be used as antibacterial and/or antifungal agents. Their effectiveness varies with the concentration of the compound used and the particular organism to be controlled.

The biocidal activity of the compounds of the present invention is demonstrated by using 2-(decylthio)ethylamine carbamic acid derivative (DTEA carbamic acid derivative) and 2-(octylthio)ethylamine carbamic acid derivative (OTEA carbamic acid derivative) as representative compounds of the invention.

The minimum inhibitory concentration (MIC) for DTEA and OTEA carbamic acid derivatives is determined for 9 bacteria, using nutrient agar, and for DTEA carbamic acid derivative for 7 yeast and fungi, using malt yeast agar. A one percent solution of DTEA or OTEA carbamic acid derivative is prepared in a mixture of acetone and water. Nutrient agar is prepared at pH 6.8 representing a neutral medium, and at pH 8.2, representing an alkaline medium. The nutrient agars are prepared by adding 23 g of nutrient agar to one-liter of deionized water. In addition, the alkaline medium is prepared by adjusting a 0.04M solution of N-[tris(hydroxymethyl)methyl]-glycine buffered deionized water with concentrated sodium hydroxide to a pH of 8.5. Malt yeast agar is prepared by adding 3 g yeast extract and 45 g malt sugar per liter of deionized water. The specific agar is dispensed in 30 ml aliquots into $25 \times 200$ mm test tubes, capped and autoclaved for 15 minutes at 115° C. The test tubes containing the agar are cooled in a water bath until the temperature of the agar is 48° C. Then, an appropriate amount of the one percent solution of the test compound is added (except in the controls where no compound is added) to the respective test tubes so that the final concentrations are 500, 250, 100, 50, 25, 10, 5, 2.5, 1.0 and 0 parts per million of the test compound in the agar, thus having a known concentration of test compound dispersed therein. Not all compounds were tested at all the concentrations. The contents of the test tubes are then transferred to respective petri plates. After drying for 24 hours, the petri plates containing nutrient agar are inoculated with bacteria and those containing malt yeast agar are inoculated with yeast and fungi.

The inoculation with bacteria is accomplished by using the following procedure. Twenty-four hour-cultures of each of the bacteria are prepared by incubating the respective bacteria in tubes containing nutrient broth for 24 hours at 30° C. in a shaker. Dilutions of each of the 24 hour-cultures are made so that nine separate suspensions (one for each of the nine test bacteria) are made, each containing $10^8$ colony forming units (CFU) per ml of suspension of a particular bacteria. Aliquots of 0.3 ml of each of the bacterial suspensions are used to fill the individual well of Steer's Replicator. For each microbial suspension, 0.3 ml was used to fill three wells (i.e., three wells of 0.3 ml each) so that for the nine different bacteria, 27 wells are filled. The Steer's Replicator is then used to inoculate both the neutral and alkaline pH nutrient agar petri plates.

The inoculated petri plates are incubated at 30° C. for 48 hours and then read to determine if the test compound which is incorporated into the agar prevented growth of the respective bacteria.

The inoculation with the yeast and fungi is accomplished as follows. Cultures of yeast and fungi are incubated for seven days on malt yeast agar at 30° C. These cultures are used to prepare suspensions by the following procedure. A suspension of each organism is prepared by adding 10 ml of sterile saline and 10 microliters ($\mu$l) of octylphenoxy polyethoxy ethanol (TRITON TM X-100, a trademark of Rohm & Haas Company) to the agar slant of yeast or fungi. The sterile saline/octylphenoxy polyethoxy ethanol solution is then agitated with a sterile swab to suspend the microorganism grown on the slant. Each resulting suspension is diluted into sterile saline (1 part suspension: 9 parts sterile saline). Aliquots of these dilutions are placed in individual wells of Steer's Replicator and petri plates inoculated as previously described. The petri plates are incubated at 30° C. and read after 48 hours for yeast and 72 hours for fungi.

Table I lists the nine bacteria and seven yeast and fungi used in the MIC test described above along with their respective American Type Culture Collection (ATCC) identification numbers.

TABLE I

| Organism Used In The Minimum Inhibitory Concentration Test | |
|---|---|
| Organism | ATCC No. |
| Bacteria | |
| Bacillus subtilis (Bs) | 8473 |
| Enterobacter aerogenes (Ea) | 13048 |
| Escherichia coli (Ec) | 11229 |
| Klebsiella pneumoniae (Kp) | 8308 |
| Proteus vulgaris (Pv) | 881 |
| Pseudomonas aeruginosa (Pa) | 10145 |
| Pseudomonas aeruginosa (PRD-10) | 15442 |
| Salmonella choleraesuis (Sc) | 10708 |
| Staphylococcus aureus (Sa) | 6538 |
| Yeast/Fungi | |
| Aspergillus niger (An) | 16404 |
| Candida albicans (Ca) | 10231 |
| Penicillium chrysogenum (Pc) | 9480 |
| Saccharomyces cerevisiae (Sc) | 4105 |
| Trichoderma viride (Tv) | 8678 |
| Aureobasidium pullulan (Ap) | 16622 |
| Fusarium oxysporum (Fo) | 48112 |

In Table II and III, the MIC values of DTEA and OTEA carbamic acid derivatives are set forth for the bacteria organisms and yeast/fungi organisms which are listed in Table I.

TABLE II

| | Minimum Inhibitory Concentrations (in ppm) for Test Compounds against Bacteria Species | | | | | | | | |
|---|---|---|---|---|---|---|---|---|---|
| | ORGANISMS | | | | | | | | |
| COMPOUND | Bs | Ea | Ec | Kp | Pv | PRD | Pa | Sc | Sa |
| DTEA Carbamic acid deriv. | | | | | | | | | |
| pH 6.8 | 10 | 25 | 10 | 50 | 10 | >50 | >50 | 10 | 25 |
| pH 8.2 | 10 | 5 | 5 | 5 | 5 | >50 | >50 | 5 | 2.5 |
| OTEA Carbamic acid deriv. | | | | | | | | | |
| pH 6.8 | 100 | 150 | 100 | 100 | 50 | 100 | 100 | 100 | 100 |
| pH 8.2 | 25 | 25 | 25 | 25 | 50 | 250 | 37.5 | 25 | 25 |

TABLE III

| | Minimum Inhibitory Concentrations (in ppm) for Test Compounds against Yeast/Fungi Species at pH 5.5 | | | | | | |
|---|---|---|---|---|---|---|---|
| | ORGANISMS | | | | | | |
| COMPOUND | An | Ca | Pc | Sc | Tv | Ap | Fo |
| DTEA Carbamic acid derivative | 250 | 250 | 250 | 250 | 50 | 250 | 250 |

What is claimed is:

1. A method for inhibiting the growth of microorganisms on a surface which comprises applying to said surface (i) a first compound corresponding to the formula:

$$RS(CH_2)_mNH_2$$

wherein R is an alkyl group containing from 6 to 16 carbon atoms and am is an integer selected from 2 to 3 and (ii) a second compound corresponding to the formula:

$$R_1S(CH_2)_nNH_2$$

wherein $R_1$ is an alkyl group containing from 6 to 16 carbon atoms and n is an integer selected from 2 or 3, wherein the first and second compounds are applied in amounts effective to inhibit the growth of microorganisms on the surface and wherein the surface is exposed to air during application of the compounds.

2. The method of claim 1, wherein R and $R_1$ are each independently an alkyl group containing from 6 to 12 carbon atoms.

3. The method of claim 1, wherein R and $R_1$ are each decyl groups.

4. The method of claim 3, wherein m and n are each the integer 2 and the first and second compounds are the same.

5. A method for inhibiting the growth of marine organisms on a surface which comprises applying to said surface (i) a first compound corresponding to the formula:

$$RS(CH_2)_mNH_2$$

wherein R is an alkyl group containing from 6 to 16 carbon atoms and m is an integer selected from 2 or 3, and (ii) a second compound corresponding to the formula:

$$R_1S(CH_2)_nNH_2$$

wherein $R_1$ is an alkyl group containing from 6 to 16 carbon atoms and n is an integer selected from 2 or 3, wherein the first and second compounds are used in amounts effective to inhibit the growth of microorganisms on the surface and wherein the surface is exposed to air during application of the compounds.

6. The method of claim 5, wherein R and $R_1$ are each independently an alkyl group containing from 6 to 12 carbon atoms.

7. The method of claim 5, wherein R and $R_1$ are each decyl groups.

8. The method of claim 7, wherein m and n are each the integer 2 and the first and second compounds are the same.

9. A method for inhibiting the growth of microorganisms on a surface which comprises introducing onto said surface at least one compound corresponding to the formula:

$$RS(CH_2)_m\overset{+}{N}H_3\overset{-}{O}-\overset{O}{\overset{\|}{C}}NH(CH_2)_nSR_1$$

wherein R and $R_1$ are each independently alkyl groups containing from 6 to 16 carbon atoms, and m and n are each independently integers selected from 2 or 3 and wherein the compound or compounds are introduced in an amount effective to inhibit the growth of microorganisms on the surface.

10. The method of claim 9, wherein R and $R_1$ are each independently an alkyl group containing from 6 to 12 carbon atoms.

11. The method of claim 9, wherein R and $R_1$ are each decyl groups.

12. The method of claim 11, wherein m and n are each the integer 2.

13. A method for inhibiting the growth of marine organisms on a surface, said method comprising introducing onto said surface at least one compound corresponding to the formula:

$$RS(CH_2)_m\overset{+}{N}H_3\overset{-}{O}-\overset{O}{\overset{\|}{C}}NH(CH_2)_nSR_1$$

wherein R and $R_1$ are each independently alkyl groups containing from 6 to 16 carbon atoms, and m and n are each independently integers selected from 2 or 3 and wherein the compound or compounds are used in an amount effective to inhibit the growth of microorganisms on the surface.

14. The method of claim 13, wherein R and $R_1$ are each independently an alkyl group containing from 6 to 12 carbon atoms.

15. The method of claim 13, wherein R and $R_1$ are each decyl groups.

16. The method of claim 15, wherein m and n are each the integer 2.

* * * * *

UNITED STATES PATENT AND TRADEMARK OFFICE
CERTIFICATE OF CORRECTION

PATENT NO. : 5,118,534

DATED : June 2, 1992

INVENTOR(S) : Attila G. Relenyi; Richard W. Walter; Charles D. Gartner

It is certified that error appears in the above-identified patent and that said Letters Patent is hereby corrected as shown below:

Column 9 line 32, "am" should read --n--. "2 to 3" should read 2 --or--3

Signed and Sealed this

Fourteenth Day of December, 1993

Attest:

BRUCE LEHMAN

Attesting Officer

Commissioner of Patents and Trademarks